US012667653B2

(12) United States Patent
Grandolfo et al.

(10) Patent No.: US 12,667,653 B2
(45) Date of Patent: Jun. 30, 2026

(54) EXTERNAL END DEVICE AND METHOD FOR ITS CONNECTION TO FLOW LINES

(71) Applicants:Nicola Grandolfo, Triggiano (IT);
Emilio Magaldi, San Mango Piemonte (IT)

(72) Inventors: Nicola Grandolfo, Triggiano (IT);
Emilio Magaldi, San Mango Piemonte (IT)

( * ) Notice: Subject to any disclaimer, the term of this patent is extended or adjusted under 35 U.S.C. 154(b) by 1021 days.

(21) Appl. No.: 17/758,802

(22) PCT Filed: Jan. 13, 2021

(86) PCT No.: PCT/IB2021/050232
§ 371 (c)(1),
(2) Date: Jul. 14, 2022

(87) PCT Pub. No.: WO2021/144716
PCT Pub. Date: Jul. 22, 2021

(65) Prior Publication Data
US 2023/0044667 A1     Feb. 9, 2023

(30) Foreign Application Priority Data

Jan. 14, 2020    (IT) ........................ 102020000000565
Jan. 14, 2020    (IT) ........................ 102020000000568

(51) Int. Cl.
*A61M 1/36* (2006.01)
*A61M 1/28* (2006.01)
(Continued)

(52) U.S. Cl.
CPC .......... *A61M 1/3653* (2013.01); *A61M 39/10* (2013.01); *A61B 5/6866* (2013.01);
(Continued)

(58) Field of Classification Search
CPC . A61B 2562/225; A61M 39/10; A61M 39/04; A61M 39/20; A61M 1/3653;
(Continued)

(56) References Cited

U.S. PATENT DOCUMENTS 4,755,173 A * 7/1988 Konopka .......... A61M 25/0606
604/122
4,874,369 A * 10/1989 Kulle .................... A61M 39/04
604/86
(Continued)

FOREIGN PATENT DOCUMENTS

CN         1969749 A      5/2007
DE     102007025900 A1 * 12/2008    ............ A61M 39/20
(Continued)

*Primary Examiner* — Bhisma Mehta
*Assistant Examiner* — Mark A Igel
(74) *Attorney, Agent, or Firm* — FisherBroyles, LLP; Roger L. Browdy; Ronni S. Jillions

(57) ABSTRACT

An external end device has a casing (4), a fitting (15) housed in the casing (4) and having at least one distal part (16) which engages a catheter (3), and two proximal tracts (17, 17), in which a pair of curved pipes (18, 18) are inserted with a distal end (180) thereof. The curved pipes (18, 18) have a proximal end (181), in which a pair of nozzles (190, 190) are inserted. Inside each nozzle (190) there is a cap (20) suitable for hermetically sealing the nozzle (190). A piercing and connecting conduit (24) is adapted to reversibly pierce the cap (20) and to connect the pair of nozzles (190, 190) to the flow lines of the treatment equipment. Also disclosed is a method of connecting the external terminal device to flow lines of a machine.

10 Claims, 6 Drawing Sheets

(51) Int. Cl.
| | | |
|---|---|---|
| *A61M 39/04* | (2006.01) | |
| *A61M 39/10* | (2006.01) | |
| *A61M 39/20* | (2006.01) | |
| *A61B 5/00* | (2006.01) | |
| *A61M 1/14* | (2006.01) | |

(52) U.S. Cl.
CPC .......... *A61B 2562/225* (2013.01); *A61M 1/14*
(2013.01); *A61M 1/285* (2013.01); *A61M*
*39/04* (2013.01); *A61M 39/20* (2013.01)

(58) Field of Classification Search
CPC ...... A61M 1/14; A61M 1/285; A61M 1/3661;
A61M 39/105
See application file for complete search history.

(56) References Cited

U.S. PATENT DOCUMENTS

| | | | | |
|---|---|---|---|---|
| 5,290,222 | A * | 3/1994 | Feng ................... | A61M 39/1011 |
| | | | | 604/905 |
| 5,386,735 | A * | 2/1995 | Langdon ................. | A61M 1/68 |
| | | | | 73/864.34 |
| 5,453,576 | A * | 9/1995 | Krivitski .............. | A61B 5/0275 |
| | | | | 600/481 |
| 6,007,516 | A * | 12/1999 | Burbank ............. | A61M 1/3656 |
| | | | | 604/245 |
| 6,206,851 | B1 * | 3/2001 | Prosl ................. | A61M 39/0208 |
| | | | | 604/93.01 |
| 7,347,853 | B2 * | 3/2008 | DiFiore ............ | A61M 39/0606 |
| | | | | 604/537 |
| 7,500,949 | B2 | 3/2009 | Gottlieb et al. | |
| 9,295,773 | B2 | 3/2016 | Prosl et al. | |
| 11,065,418 | B1 * | 7/2021 | Brody ................... | A61M 39/22 |
| 2001/0020153 | A1 * | 9/2001 | Howell ................. | A61M 39/04 |
| | | | | 604/167.03 |
| 2004/0019312 | A1 * | 1/2004 | Childers ............... | A61M 1/154 |
| | | | | 604/4.01 |
| 2005/0113658 | A1 * | 5/2005 | Jacobson ............. | A61B 5/4839 |
| | | | | 600/316 |
| 2008/0015487 | A1 * | 1/2008 | Szamosfalvi ....... | A61M 1/3413 |
| | | | | 210/323.1 |
| 2009/0156975 | A1 * | 6/2009 | Robinson ............. | A61B 5/4839 |
| | | | | 210/636 |
| 2011/0046457 | A1 * | 2/2011 | Gottlieb ............ | A61M 25/0032 |
| | | | | 29/428 |
| 2011/0184259 | A1 | 7/2011 | Alarcon et al. | |
| 2011/0270046 | A1 * | 11/2011 | Paul ......................... | A61B 5/68 |
| | | | | 604/533 |
| 2012/0089096 | A1 * | 4/2012 | Grandolfo ........... | A61M 1/3661 |
| | | | | 604/175 |
| 2012/0157924 | A1 * | 6/2012 | Schutz .................. | A61M 39/26 |
| | | | | 604/175 |
| 2013/0303986 | A1 * | 11/2013 | Penalosa, Jr. ..... | A61M 25/0097 |
| | | | | 604/118 |
| 2014/0024998 | A1 * | 1/2014 | Prosl ................... | A61M 1/3655 |
| | | | | 604/27 |
| 2015/0018641 | A1 | 1/2015 | Alarcon et al. | |
| 2015/0025468 | A1 * | 1/2015 | Grandolfo ........... | A61M 1/3653 |
| | | | | 604/173 |
| 2017/0045170 | A1 * | 2/2017 | Lewis ................... | A61M 39/10 |
| 2019/0111235 | A1 * | 4/2019 | Jones ................. | A61M 39/284 |
| 2021/0069404 | A1 * | 3/2021 | Raval ............. | A61M 1/3656 |
| 2021/0299408 | A1 * | 9/2021 | Yong ................. | A61M 25/0606 |

FOREIGN PATENT DOCUMENTS

| | | | | | |
|---|---|---|---|---|---|
| ES | 2336123 | T3 * | 4/2010 | ................ | F04B 7/04 |
| WO | 2006044973 | A1 | 4/2006 | | |
| WO | WO-2010146614 | A2 * | 12/2010 | ......... | A61M 1/3659 |
| WO | 2013108280 | A2 | 7/2013 | | |
| WO | WO-2019088360 | A1 * | 5/2019 | ........... | A61M 39/02 |

\* cited by examiner

EXTERNAL END DEVICE AND METHOD FOR ITS CONNECTION TO FLOW LINES

TECHNICAL FIELD

The present invention relates to an external end device usable for example in hemodialysis, peritoneal dialysis and chemotherapy. The invention also describes a method of connecting the external end device to flow lines of a treatment equipment.

BACKGROUND ART

U.S. Pat. No. 6,969,381 B2 discloses a two-part separable hemodialysis device: a part distal to the flow lines of a hemodialysis machine, which is connected to a two-lumen catheter implanted in a patient and is fixed with suture stitches thereto; a proximal part, which can be attached to the two-lumen catheter and has respective extension pipes ending with proximal luer connectors for connection to the flow lines. A flow blocking clamp is provided on each of the extension pipes.

When the proximal part of the device is separated from the distal part, the latter remains open and therefore susceptible to getting dirty and becoming infected. If the proximal and distal parts are kept together, the patient is forced to wear both even when the device is disconnected from the hemodialysis machine. Also in this case, the luer connectors are exposed to the outside and subject to getting dirty.

WO/2010/146614 discloses an external end device for permanent catheters, comprising a container connectable on one side to at least one catheter, and on the other side to a closure lid containing a disposable absorbent material impregnated with an antiseptic substance. This container houses two taps equipped with knobs that can be operated from the outside. The two taps are equipped, on one hand, with first terminals for connection to the catheters and, on the other, with second terminals protruding from the container for connection to external equipment. The first terminals are connected to the catheters, which come out of the container through at least one non-rigid support sleeve, in turn integral with the container. The support sleeve externally carries a cuff intended to be positioned in the subcutaneous tissue of a patient's body. The second terminals are provided with caps surrounded by the disposable absorbent material, located in the closing lid. The closing lid makes the absorbent material adhere to the caps and covers them to protect them externally from bacterial attack, also using the antiseptic substance with which it is impregnated. The knobs positioned outside the container operate the taps connected to the catheters. Each tap moves a ball body that is located inside a respective conduit connected to the catheter, and opens and closes, if necessary, the flow of blood.

The ball bodies are a foreign material crossed by the blood which is stressed by the friction in the ball body crossing and by the interruption of the flow by the same.

To overcome this, WO/2013/108280 discloses an external end device for permanent catheters, in which two sleeve valves and two elastic pipes acting as valve sleeves replace the taps of the device disclosed by WO/2010/146614. The device according to WO/2013/108280 avoids the mechanical actuation of the tap on the blood, but does not exclude the stresses on the blood caused by the crushing by vertical elements which, acting on the two elastic pipes, interrupt the flow of blood when the patient is disconnected from the hemodialysis treatment equipment or the like.

An access system for hemodialysis treatment is described by U.S. Pat. No. 9,295,773 B2, whose applicants, founders of Biolink, contributed to the development of the product known as Dialock. The system described by the aforementioned patent comprises an interfacial fluid conduit between the machine and patient's blood supply. This can be connected repeatedly along a guided path passing through the epidermis and subcutaneous tissue. The device described by U.S. Pat. No. 9,295,773 B2, while possessing considerable advantages, requires the installation of a subcutaneous port and also the perforation of the patient's skin repeated at each hemodialysis treatment.

SUMMARY OF THE INVENTION

The present invention aims to overcome the drawbacks and difficulties mentioned above.

An object of the invention is to provide an external end device for one or two permanent catheters which improves their isolation from the environment and, therefore, from the attack of pathogens, as well as the isolation of their opening and closing means.

Another object of the invention is to eliminate the frictional stresses, or "shear stress", caused on the blood.

A further object of the invention is to provide an end device that does not have taps or valves and therefore does not require the verification of their actual closed position.

An additional object of the invention is to provide an end device that permits to detect an analyte concentration in the patient's blood.

In a first aspect of the invention, an external end device is provided as described in claim 1 and in the claims dependent on it.

In a second aspect of the invention, a method of connecting the external end device to flow lines of a treatment equipment is provided as defined in claim 11

BRIEF DESCRIPTION OF DRAWINGS

Further features and advantages will become most evident in the present description of embodiments of an external end device, illustrated by way of non-limiting example with the aid of the attached drawings in which.

DESCRIPTION OF PREFERRED EMBODIMENTS OF THE INVENTION

Figure 1:
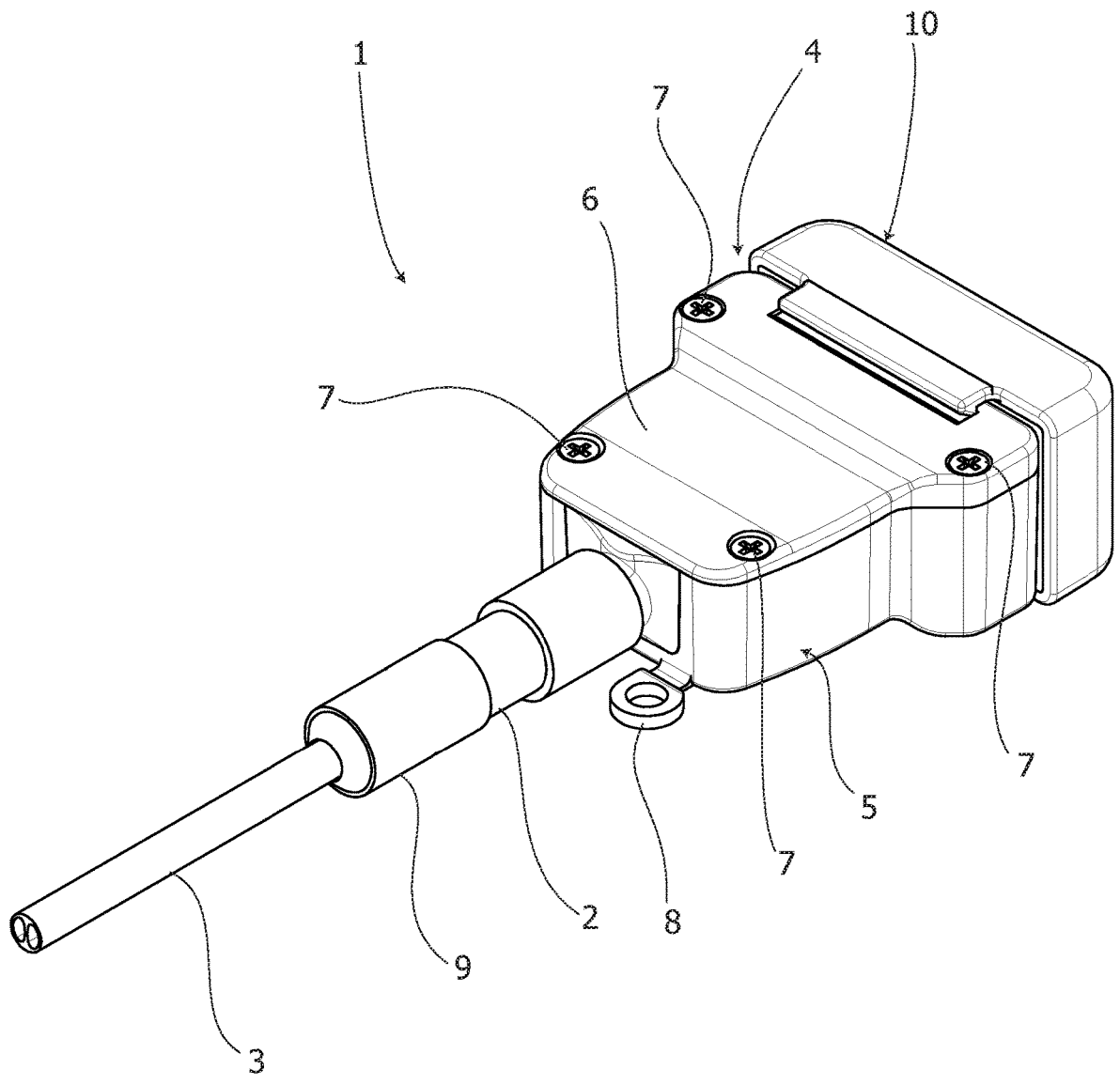
FIG. 1 shows a general perspective view of a first embodiment of the device according to the invention, in the closed position.

Reference is made to FIG. 1, which is a general perspective view of a first embodiment of the external end device according to the invention, in closed position, i.e. not connected to the flow lines of a blood treatment equipment. The external end device, generally indicated as 1, is joined to a two-lumen catheter 3 implanted in a patient, in the following catheter 3. The catheter 3 passes through a tubular coating 2 adapted to anchor the end device external to the patient. The external end device 1 comprises a casing 4, including a base 5 and a removable cover 6, fixed with screws, generally indicated as 7, to the base 5. Integrated in the base 5 are two rings 8 (only one is visible in FIG. 1) for sewing the external end device 1 to the patient's skin. A cuff 9 is applied to the tubular coating 2 and is intended to be placed in the subcutaneous position. The casing 4 is closed with a lid 10 better visible in FIG. 2, which shows an exploded perspective view of the external end device 1 in FIG. 1, complete with a piercing and connecting conduit to be connected to flow lines of an apparatus treatment for hemodialysis (not shown).

The base 5 comprises side walls 50 on which the removable cover 6 is fixed by means of the screws 7 with the interposition of a gasket 11. In the side walls 50, the base 5 has a distal opening 12 with respect to the flow lines of a treatment apparatus for hemodialysis and a pair of proximal openings 13, 13.

Figure 2:
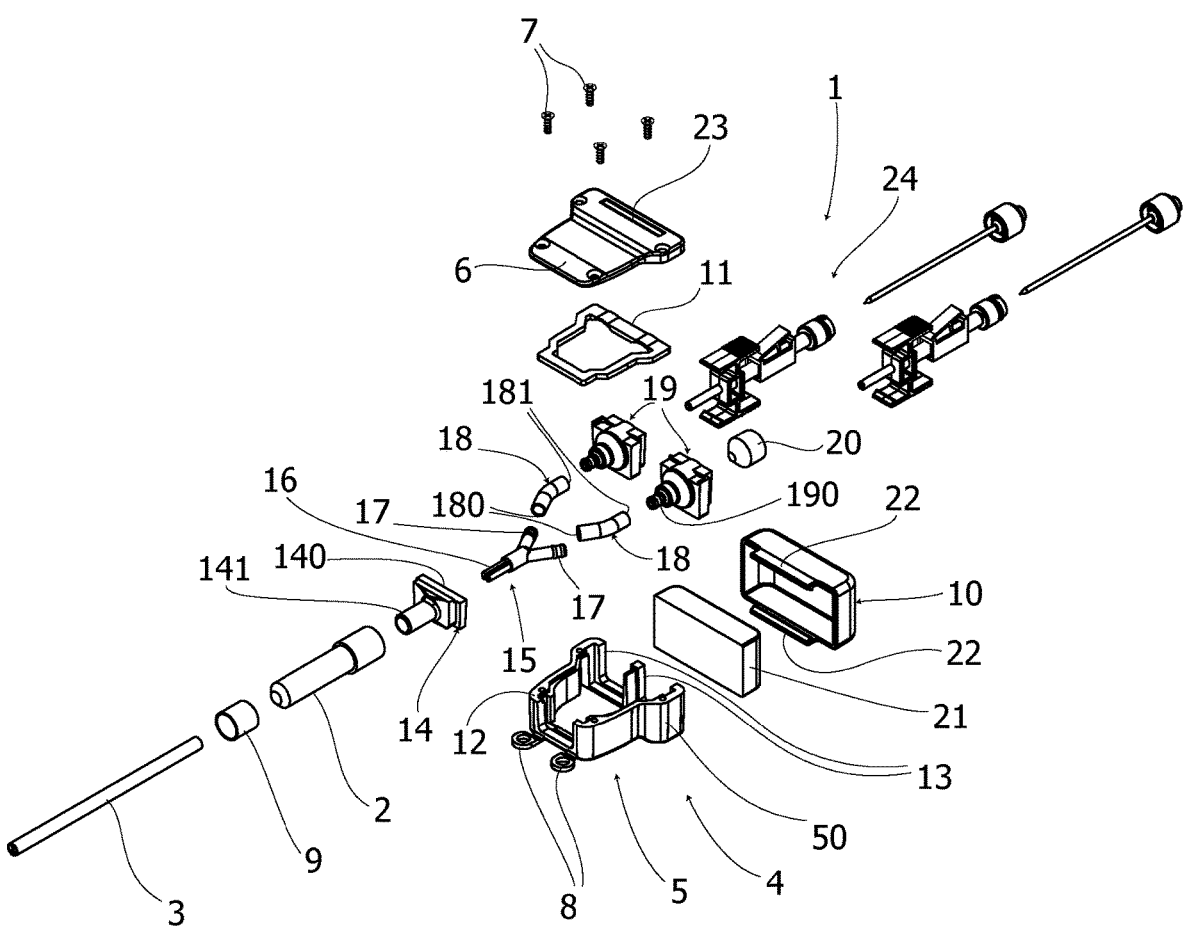
FIG. 2 shows an exploded perspective view of the external end device in FIG. 1, complete with a piercing and connecting conduit to be connected to the flow lines of a treatment apparatus for hemodialysis.
Figure 3:
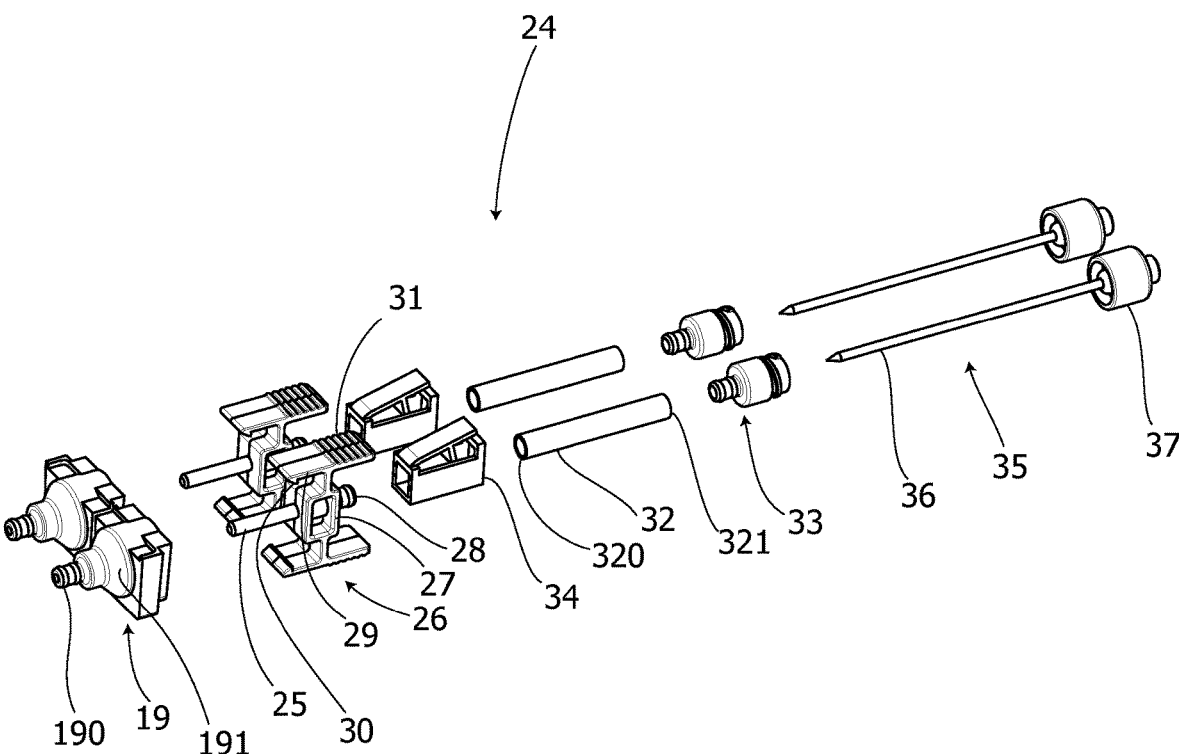
FIG. 3 shows a partial exploded perspective view on an enlarged scale of FIG. 2, especially of the piercing and connecting conduit.

The distal opening 12 and the proximal openings 13, 13 are delimited on three sides by grooves designed to form guides for the insertion of septa. In particular, the distal opening 12 provides for the insertion of a perforated septum 14, equipped with a wall 140 and a tubular trunk 141 passing through the wall 140. The catheter 3 passes through the tubular trunk 141 in order to engage a fitting 15 which is located within the base 5. A distal part 16 of fitting 15 is generally a two-lumen catheter tract that engages the catheter 3. Two proximal tracts 17, 17 of fitting 15 fit into a distal end 180 of curved pipes 18, 18. In the proximal end 181 of the curved pipes 18, 18 are inserted nozzles 190, 190 connected with respective nozzle chambers 191, 191, as shown in FIG. 3 that is a partial exploded perspective view on an enlarged scale of FIG. 2, especially of the piercing and connecting conduit. The nozzle chambers 191, 191 are received in through septa 19, 19 intended to be retained in the proximal openings 13, 13 of the walls 50 of the casing 4. The nozzle chambers 191, 191, have a substantially cylindrical shape tapered towards the nozzles 190, 190. A cap 20 is inserted inside each nozzle chamber 191 as shown in FIGS. 2 and 3.

The cap 20 is reversibly pierceable, of a substantially cylindrical shape tapered distally, like the nozzle chamber 191. Reversibly pierceable feature means that the cap 20 can be perforated by a piercing member and return perfectly sealing after extraction of the piercing member. The reversibly pierceable cap 20 may be made of silicone or other suitable material.

In this way, when the external end device 1 is not in use, the silicone cap 20 perfectly closes the passage of the nozzle 190, and the casing 4 is closed by the lid 10 with the interposition of an antiseptic sponge 21. The lid 10 has distal projections 22, 22, the ends of which engage corresponding recesses indicated as 23 in the removable cover 6 and a similar recess (not shown) created externally in the bottom wall of the base 5 of the casing 4.

Figure 4:
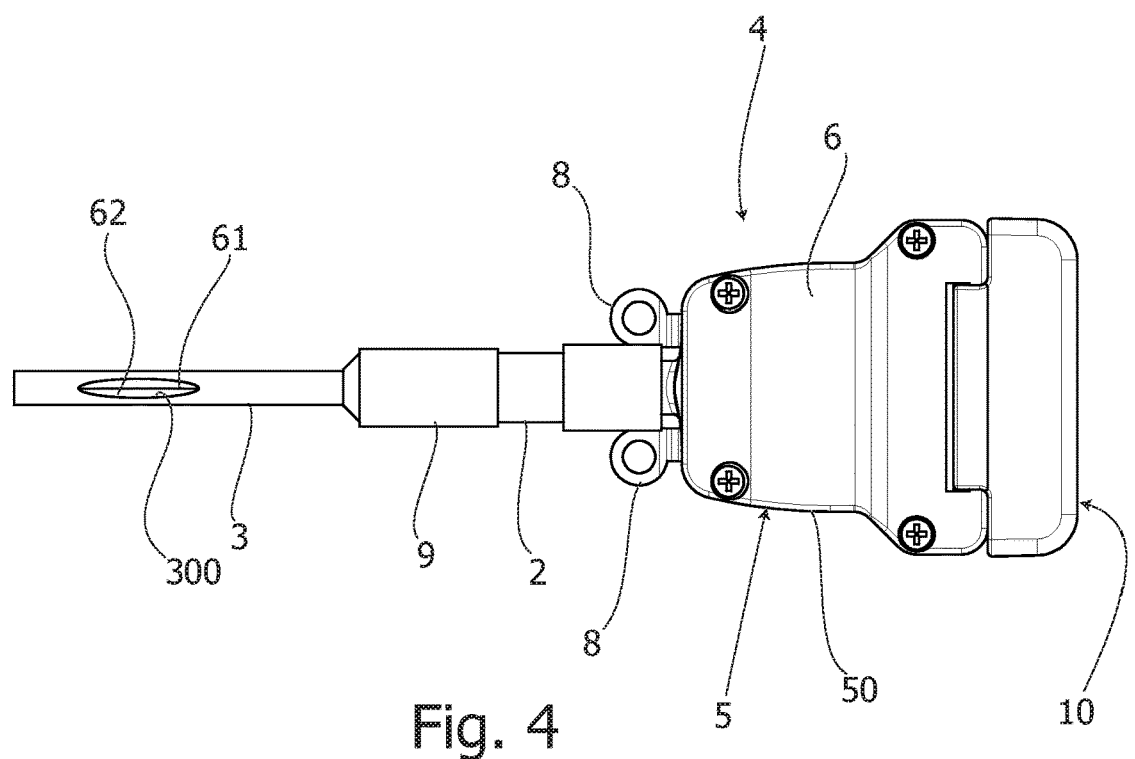
FIG. 4 is a top plan view of a second embodiment of the external end device according to the present invention.
Figure 5:
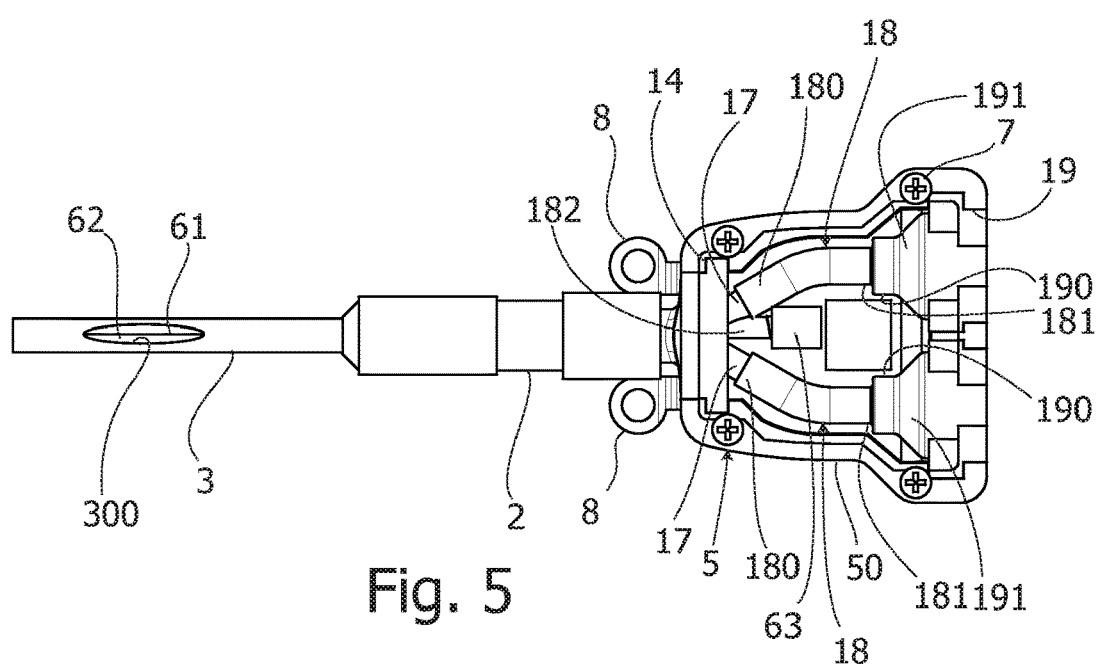
FIG. 5 is a top plan view of the second embodiment of the external end device in FIG. 4, without removable cover and lid, in order to show the inside of the device.
Figure 6:
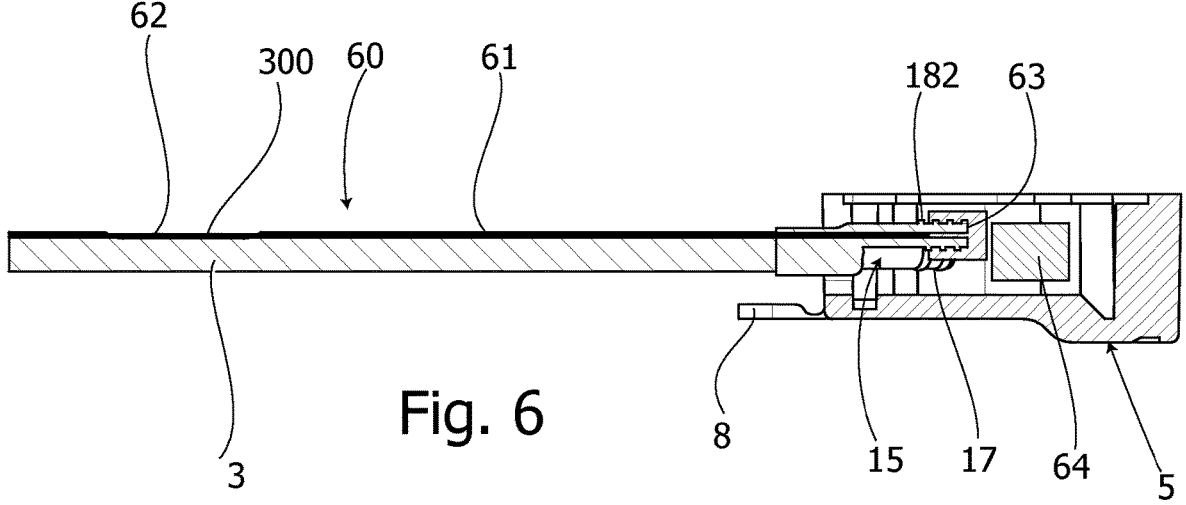
FIG. 6 shows a longitudinal cross-section view, with parts removed for clarity, of the device in FIG. 5.
Figure 7:
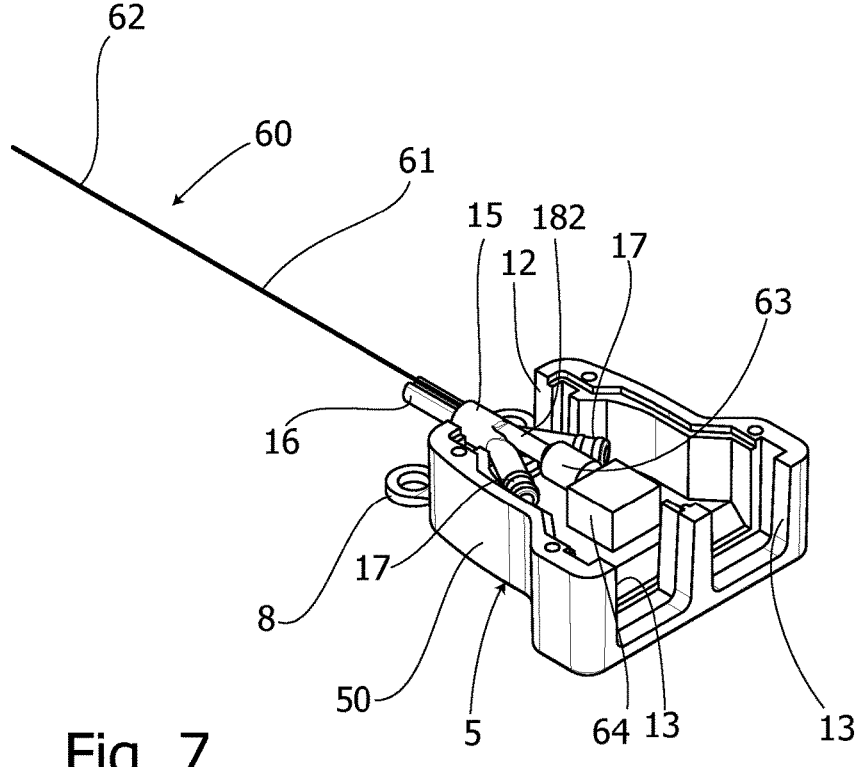
FIG. 7 shows a perspective view corresponding to FIG. 6.

Reference is made now to FIGS. 4 and 5 that are top plan views of a second embodiment of the external end device, the FIG. 5 showing the device without removable cover and lid. Further, reference is made to FIGS. 6 and 7 which show a longitudinal cross-section view and a perspective view, respectively, of the device in FIG. 5, with parts removed for clarity.

According to the second embodiment of the invention, the external end device comprises a biosensor 60 having a sensitive element 62. For this purpose, provided in the catheter 3 is a transparent window 300 facing the sensitive element 62 of the biosensor 60 so that the sensitive element 62 is in view of the blood that laps the catheter 3. The fitting 15 includes, in addition to the two proximal tracts 17, 17, an access conduit 182 to the catheter 3, inside which the biosensor 60 is partially arranged. The biosensor 60 comprises an optical fiber 61 at the end of which the sensitive element 62 is arranged. The optical fiber 61 is inserted through the access conduit 182. An optical system 63 is connected to the optical fiber 61. The biosensor 60 is able to detect an analyte sought in the blood thanks to the optical reaction of its sensitive element according to known techniques.

A detection and transmission system 64 of what has been revealed is also provided. The detection and transmission system 64 is a microprocessor which manages signal processing, mathematical manipulation of the same and data storage. The detection and transmission system 64 can be in physical or wireless connection. The optical system 63 includes a variable wavelength light source that allows various substances dissolved in the blood, that have a different level of reactivity to the wavelength of the light supplied, to be scanned. In order to carry out what has been described, reference is made to WO 2006/044973, which describes an optical fiber suitable for detecting the concentration of analytes, in particular the concentration of glucose in the blood of a patient.

Figure 8:
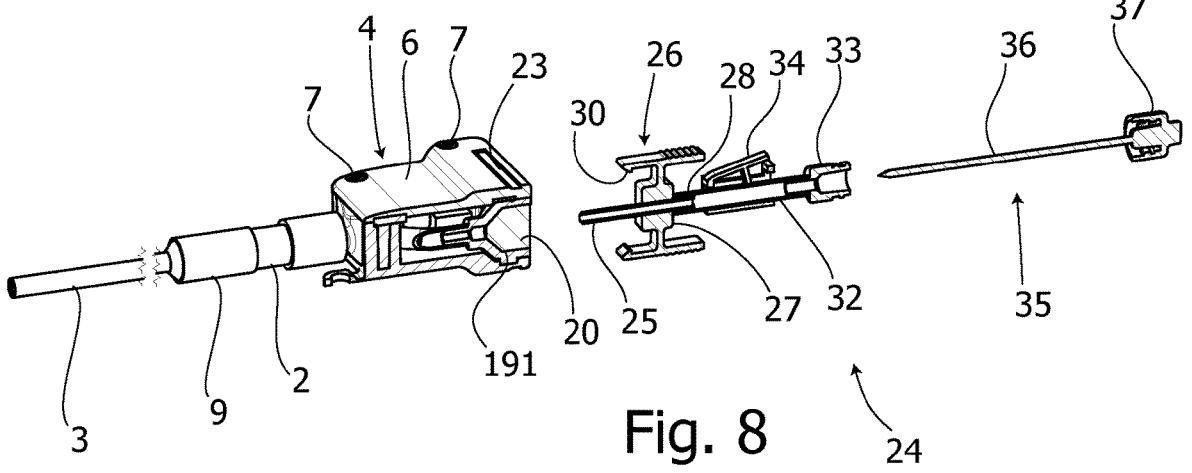
FIGS. 8 and 9 show exploded longitudinal cross-sections view in an exploded view and in the assembled condition, respectively, along a flow line of the piercing and connecting conduit in FIG. 3.
Figure 9:
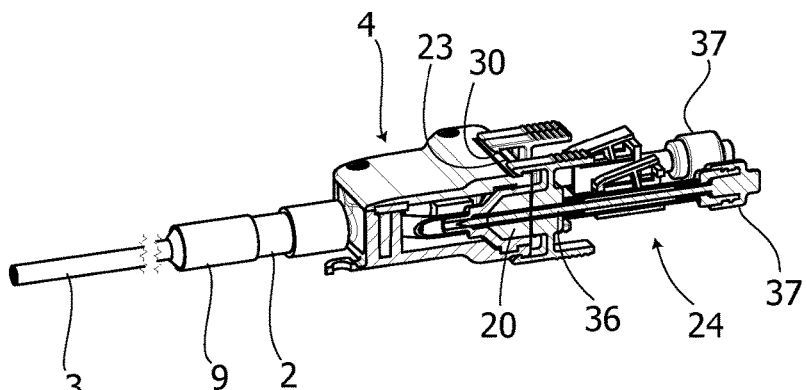

Reference is made now to FIG. 3 and FIGS. 8 and 9, which show an exploded longitudinal cross-section view and an exploded longitudinal cross-section view in assembled condition, respectively, along only one flow line of the piercing and connecting conduit in FIG. 3.

The reference numerals in FIG. 3 are indicated, for clarity sake, only on one part of this conduit, the other part being identical.

As will be said later in exposing the method, when the external end device 1 is to be connected to the lines of the hemodialysis treatment apparatus, the lid 10 and the antiseptic sponge 21 are removed. Then, through the caps 20 of the external end device, passages are made for the blood by means of a piercing and connecting conduit 24. The piercing and connecting conduit 24 comprises, starting distally, a pair of rigid pipes 25, 25 mounted on respective clamps 26, 26. Each clamp 26 comprises a central body 27 centrally perforated in order to create a connection between the rigid pipe 25 and a joint 28 located in the central body 27 on the opposite side to the rigid pipe 25. Provided above and below the central body 27 are gripper arms 29, 29 which distally have a hook 30 for retaining the casing 4. The gripper arms 29, 29 are sized so as to engage, on opposite sides to the central body 27, the recesses 23 made in the removable cover 6 and in the base 5. A stable connection of the piercing and connecting conduit 24 to the casing 4 is thus obtained, and therefore to the flow lines of the treatment equipment.

On the opposite side to the gripper arms 29, 29, i.e. in the proximal tract, there is a gripping lever 31, suitably knurled externally.

On the joint 28 there is inserted a distal end 320 of an elastic pipe 32 which, at its proximal end 321, is joined to a respective lock element, such as a luer lock, indicated as 33, for an attachment to the flow lines. An occlusion clip 34 is positioned on each elastic pipe 32. A piercing member 35 for each flow line completes the piercing and connecting conduit 24. Each piercing member 35 has a needle 36 and an internally hollow head 37 to close on the lock element 33.

FIG. 8 shows, for simplicity, a single piercing and connecting conduit 24 in which the clamp 26 is connected to the elastic pipe 32, which, after the insertion of the occlusion clip 34, is, in turn, connected to the lock element 33. The piercing member 35 is shown separate.

As shown in FIG. 9, the piercing and connecting conduit 24, once completely assembled, is approached to the external end device so that the tip of each needle 36, passing through the lock element 33, the elastic pipe 32, the joint 28, the central body 27 of the clamp 26, and the rigid pipe 25, pierce the cap 20 located inside the nozzle chamber 191 of the through septum 19. When the gripper arms 29, 29 engage the nozzles of the through septa 19 with the hooks 30, each cap 20 is pierced and inside it passes a rigid pipe 25, coaxial to the needle 36. In this way a connection is created between the flow lines of the treatment apparatus and the nozzles 190, 190, when the piercing members 35, 35 are extracted and the lock elements 33, 33 are connected to the flow lines of the hemodialysis treatment apparatus. The occlusion clips 34, 34, which were closed on the elastic pipes 32, 32 before the insertion of the piercing members 35, 35, can open and the treatment can begin.

At the end of the treatment, the occlusion clips 34, 34 are closed, and the piercing and connecting conduit 24 is extracted from the external end device 1. During extraction, the rigid pipes 25, 25 come out of the respective caps 20 which close hermetically to their exit. In this way the leakage of blood is prevented, and the envelope 4 of the external end device 1 can be closed with the antiseptic sponge 21 and the lid 10.

Briefly, a method for connecting the external end device to the flow lines of a treatment equipment according to the present invention comprises the following steps:

removing the lid 10 and the antiseptic sponge 21 from the casing 4 of the external end device;

in-line assembling the piercing and connecting conduit 24 by joining the pair of clamps 26, 26, the pair of elastic pipes 32, 32, the pair of occlusion clips 34, 34, around the respective elastic pipes 32, 32, the pair of lock elements 33, 33, and the pair of piercing members 35, 35;

approaching the piercing and connecting conduit 24 thus mounted coaxially to the pair of nozzles 190, 190 until the coupling of the pair of clamps 26, 26 to the casing 4 with consequent reversible piercing of the caps 20 inside the chambers 191, 191 of nozzle;

removing the pair of piercing members 35, 35 from the piercing and connecting conduit 24 with simultaneous closing of the pair of occlusion clips 34, 34 around the pair of elastic pipes 32, 32; and 1 connecting the pair of lock elements 33, 33 to the flow lines of the treatment equipment.

It should be understood that the intended purposes have been achieved. The external end device according to the present invention has performances and efficiency close to those described in US 9,295,773 B2, but with the advantage that the patient's skin must not be pierced at each connection with the treatment equipment. The performance is guaranteed by the hermetic seal of the envelope 4 and by the minimization of the patient's blood contact with the outside with a consequent decrease in the dangers of infection.

The invention claimed is:

1. An external end device adapted to be connected, on one side, to at least one catheter, on which a subcutaneous cuff is applied, and, on the other side, to a lid, or alternatively to flow lines of a treatment apparatus, the external end device comprising:

a casing, including a base delimited by a plurality of side walls, in which there are a distal opening and a pair of proximal openings with respect to said flow lines, and a removable cover on the side walls, a fitting housed in the casing and having at least one distal part that engages in the at least one catheter, and two proximal tracts, and a pair of curved pipes each having a distal end inserted on the respective proximal tract of the fitting, and a proximal end, a pair of nozzles equipped with nozzle chambers and inserted in the proximal end of the curved pipes, inside each nozzle chamber being a cap that is adapted to hermetically close the nozzle and is reversibly pierceable, and a piercing and connecting conduit designed to reversibly pierce the cap and to connect the pair of nozzles to the flow lines of the treatment equipment, wherein the piercing and connecting conduit comprises in parallel lines, starting from a distal end of the piercing and connecting conduit:

a pair of clamps, each clamp having a central body centrally perforated in line, a rigid pipe intended to be connected to a respective nozzle in the septum, and a joint located in the central body on the opposite side of the rigid pipe, a pair of elastic pipes, each elastic pipe having a distal end, inserted on the joint, and a proximal end, a pair of lock elements, each lock element being connected, on one side, to the proximal end of the elastic pipe and, on the other side, to the connection to the flow lines of the treatment equipment, a pair of occlusion clips, each occlusion clip being positioned around each elastic pipe, and a pair of piercing members, each piercing member having a needle and a head internally hollow to close on the lock element, the needle passing through the lock element, the elastic pipe, the clamp, to exit from the distal end of the rigid pipe.

2. The device according to claim 1, wherein the lid has distal projections, and the base of the casing and the removable coverage have recesses, which the distal projections of the lid are able to engage in closing the device with the interposition of an antiseptic sponge between the nozzle chambers closed with the caps and the lid.

3. The device according to claim 1, wherein the distal opening and the proximal openings are delimited on three sides by grooves suitable to constitute guides for inserting septa, a perforated septum for the passage of the at least one catheter and the attachment thereof to the fitting being received in the distal opening, and a pair of septa housing the pair of nozzle chambers being received in the respective proximal openings.

4. The device according to claim 1, wherein the base of the casing and the removable cover have recesses, and the pair of clamps has, on opposite sides to the central body, gripper arms distally equipped with respective hooks suitable for engaging said recesses for the stable connection of said piercing and connecting conduit to the casing.

5. The device according to claim 1, wherein the reversibly pierceable cap is made of silicone.

6. The device according to claim 1, wherein the fitting includes, in addition to the two proximal tracts, an access conduit to the at least one catheter, and a biosensor is partially inserted in the access conduit, the biosensor having a sensitive element capable of optically reacting with the blood lapping the at least one catheter.

7. The device according to claim 6, wherein the biosensor comprises a sensitive element fixed to an optical fiber received in the at least one catheter through the access conduit, an optical system connected to the optical fiber and including a light source having a variable wave length, and a detection, storage and transmission system.

8. The device according to claim 7, wherein the at least one catheter has a transparent window configured to face the sensitive element of the biosensor.

9. The device according to claim 1, in which the removable cover is fastened on the side walls by means of screws with the interposition of a gasket.

10. A method for connecting an external end device to flow lines of a treatment equipment, the external end device comprising:

a casing, including a base and a removable cover, and a lid with the interposition of an antiseptic sponge, a pair of nozzles equipped with nozzle chambers and connected in a distal end to at least one catheter through a fitting, inside each nozzle chamber being a cap suitable for hermetically closing the nozzle that is reversibly pierceable, a piercing and connecting conduit adapted to reversibly pierce the cap and to connect the pair of nozzles to the flow lines of the treatment equipment, the piercing and connecting conduit comprising in parallel lines, starting from a distal end of the piercing and connecting conduit:

a pair of clamps for hooking the piercing and connecting conduit to the casing, a pair of elastic pipes, a pair of lock elements, connectable to the flow lines of the treatment equipment, a pair of occlusion clips, positioned around each elastic pipe, and a pair of piercing members, each piercing member having a needle and a head that is internally hollow to close on the lock element, the needle passing through the lock element, the elastic pipe, the clamp, to exit from the distal end of the rigid pipe, the method comprising:

removing the lid and the antiseptic sponge from the casing;

in-line assembling the piercing and connecting conduit by joining the pair of clamps, the pair of elastic pipes, the pair of occlusion clips around respective elastic pipes, the pair of lock elements, and the pair of piercing members;

approaching the mounted piercing and connecting conduit coaxially to the pair of nozzles up to the coupling of the pair of clamps to the casing with consequent reversible piercing of the caps inside the nozzle chambers;

removing the pair of piercing members from the piercing and connecting conduit with simultaneous closing of the pair of occlusion clips around the pair of elastic pipes; and connecting the pair of lock elements to the flow lines of the treatment equipment.

* * * * *